United States Patent [19]

Robert

[11] Patent Number: 5,102,528
[45] Date of Patent: Apr. 7, 1992

[54] AG₂S MEMBRANE, PROCESS FOR ITS PREPARATION AND PROCESS FOR ITS USE IN DETECTING SILVER OR HALIDE IONS IN SOLUTION

[75] Inventor: Philippe G. Robert, Givry, France

[73] Assignee: Eastman Kodak Company, Rochester, N.Y.

[21] Appl. No.: 650,146

[22] Filed: Feb. 4, 1991

[51] Int. Cl.⁵ .................................................. G01N 26/27
[52] U.S. Cl. ................................ 204/419; 204/416; 204/153.19
[58] Field of Search .................... 204/416, 419, 153.1, 204/153.19

[56] References Cited

U.S. PATENT DOCUMENTS

| | | | |
|---|---|---|---|
| 3,563,874 | 10/1967 | Ross et al. | 204/419 |
| 3,672,962 | 12/1968 | Frant et al. | 204/419 |
| 3,809,636 | 2/1972 | Higashiyama et al. | 204/419 |
| 3,915,831 | 10/1975 | Riseman et al. | 204/419 |
| 4,040,928 | 8/1977 | Kraus et al. | 204/419 |
| 4,096,049 | 6/1978 | Van de Leest et al. | 204/419 |
| 4,172,778 | 10/1979 | Van de Leest et al. | 204/419 |
| 4,211,623 | 7/1980 | Ross, Jr. et al. | 204/419 |
| 4,317,879 | 3/1982 | Busby et al. | 204/416 |
| 4,549,953 | 10/1985 | Driscoll et al. | 204/419 |
| 4,578,173 | 3/1986 | Seshimoto et al. | 204/416 |
| 4,758,325 | 7/1988 | Kanno et al. | 204/416 |

Primary Examiner—John Niebling
Assistant Examiner—Bruce Bell
Attorney, Agent, or Firm—Carl O. Thomas

[57] ABSTRACT

The invention relates to an Ag₂S crystalline membrane, a process for its manufacture, and a process for its use in detecting silver ions or halide ions.

The membrane according to the invention comprises silver sulfide doped with an ion capable to form either with Ag⁺ or with S²⁻ a salt much more insoluble than the species in solution. Preferably the membrane further contains an inert hydrophobic compound. The membrane is prepared by coprecipitating silver sulfide with the doping agent, by homogenizing the coprecipitate with the hydrophobic compound and by pressing.

The membrane can be used in an electrode to detect silver or halide ions in solution.

13 Claims, 5 Drawing Sheets

AG₂S MEMBRANE, PROCESS FOR ITS PREPARATION AND PROCESS FOR ITS USE IN DETECTING SILVER OR HALIDE IONS IN SOLUTION

FIELD OF THE INVENTION

The invention concerns a membrane sensitive to silver ions and halide ions, useful in an electrode. More specifically, the invention relates to a crystalline membrane comprising silver sulfide useful in an electrode to determine the activity of silver or halide ions in solution.

BACKGROUND—ION SELECTIVE ELECTRODES

Ion-selective electrodes are well known in the patent literature.

In general, said electrodes comprise a crystalline membrane in the form of a pressed pellet of a material sensitive to the ion the activity of which is to be determined, located at the lower end of the electrode housing. The inner surface of the membrane is connected to the electrochemical cell arrangement through a reference element made either of an internal electrolyte of known activity in which the metal reference electrode is immersed, or through an appropriate metal system. The outer surface of the membrane is contacted with the test solution. Between both surfaces of the membrane, a potential difference is created. This potential is measured by means of a high impedance voltmeter connected to the reference element and to the test solution. The potential difference such measured and the logarithm of the activity of the ions to detect are linked by a linear relationship, the well known Nernst equation.

Numerous membranes comprised of metal sulfides, in particular $Ag_2S$ membranes are disclosed in the art.

U.S. Pat. No. 3,591,464 discloses a crystalline membrane comprised of an intimate mixture of $Ag_2S$ and another compound selected according to the nature of the ion the activity of which is to be determined. For example, to detect $Cu^{+2}$ ions, mole percentage ratios of cupric sulfide to silver sulfide are in the range of 95% CuS/5% $Ag_2S$ to 1% CuS/99% $Ag_2S$. Thus, CuS, PbS, CdS and AgSCN are associated to $Ag_2S$ to detect $Cu^{++}$, $Pb^{++}$, $Cd^{++}$ and $SCN^-$, respectively.

U.S. Pat. No. 4,400,243 discloses a membrane comprising a mixture of at least four metal sulfides, each of them corresponding to a metal ion the activity of which is to be determined. For example, the mixture consists of from 15 to 65% by weight of silver sulfide, 15 to 65% by weight of cadmium sulfide, 30 to 65% by weight of lead sulfide and 3 to 9% of copper sulfide. The mixture can be obtained by coprecipitation, for example by adding to a sodium sulfide solution a mixed solution containing 0.3 mol cadmium nitrate, 0.3 mol lead nitrate, 0.3 mol silver nitrate and 0.1 mol copper nitrate. The membrane allows the detection of $Ag^+$, $Cd^{++}$, $Pb^{++}$, $Cu^{++}$ ions.

U.S. Pat. No. 3,563,874 discloses an imporous membrane comprised of a mixture of silver sulfide and at least 5 mol percent silver halide, for example silver chloride to detect $Cl^-$; the preferred mixtures permit a variation between 10 mol percent AgCl to 90 mol percent AgCl. In the case of mixed iodide sulfide and bromide sulfide membranes, the minimum halide content should be above 5 mol percent.

U.S. Pat. No. 4,096,049 discloses a membrane made of silver sulfide and which is superficially converted into a hardly soluble substance which has one ion in common with the ion to be detected, for example AgCl, AgBr or AgI to detect $Cl^-$, $Br^-$, $I^-$, respectively.

U.S. Pat. No. 4,172,778 discloses a $Ag_3SBr$ or $Ag_3SI$ membrane to detect $Ag^+$, $I^-$ or $Br^-$. For example, $Ag_3SI$ is obtained by precipitating equimolar quantities of sodium sulfide and sodium iodide with of a slight excess of silver nitrate.

U.S. Pat. No. 3,672,692 discloses a $Ag_2S$ membrane for detecting sulfide ions in solution. Said patent teaches that the silver sulfide membrane must be of a relatively high state of purity since the presence of foreign ions or molecules, such as AgO, tends to cause porosity and poor mechanical properties.

U.S. Pat. No. 3,809,636 teaches to employ silver sulfide and silver selenide and/or telluride in combination in forming a silver ion sensing electrode, to detect silver ions. For example the membrane contains 10 to 30 wt percent of silver sulfide and 70 to 90 wt percent of silver telluride.

U.S. Pat. No. 4,549,953 discloses the combination of silver sulfide, silver selenide, silver telluride, and mercury sulfide, for example $Ag_4SSe$ or $Ag_4STe$ obtained by coprecipitation to form a membrane for measuring the activity of one of the three elements which compose the membrane.

As a summary, the $Ag_2S$ crystalline membranes of the prior art comprise a mixture of silver sulfide and of a sulfide of another metal to detect silver or said other metal, or a mixture of silver sulfide and halide salt to detect said halide.

BACKGROUND—PREFERRED PROCESS OF USE

During the precipitation of silver halides, it is useful to know the salt excess in the precipitation reactor by a potential measurement (VAg) which is related to the silver ion activity in solution, to monitor the precipitation, as explained in "*The Theory of the Photographic Process*, Fourth Edition, Edited by T. H. James, p. 5 Section F".

The prior art most common electrodes to measure said potential (VAg) are Ag/AgX electrodes made of a silver billet coated with silver halide. Such electrodes exhibit the drawback that their use is only appropriate in pure halide solutions. Their response is deviated in the presence of small amounts of heavy halide in a solution of a lighter one (bromide or iodide in chloride solution, iodide in bromide solution). Consequently this type of electrode does not give good results in mixed silver halide emulsions, unless the amount of interfering ions is very low. For example, the response of an Ag/AgBr electrode is erroneous upon an introduction of iodide.

Moreover, Ag/AgX electrodes must be regularly recleaned and replated, certain anions adsorbing strongly onto said electrodes, which can result irreversibly in erroneous responses.

Electrodes having a silver sulfide crystalline membrane are commercially available, and allow to measure the ionic activity of silver ions in solution. Such electrodes are less sensitive to interferences of other anions, such as halide ions, or to interferences of oxidizing or reducing agents present in the emulsion, however they remain very expensive.

An object of the present invention is to provide a novel Ag₂S crystalline membrane sensitive to silver ions and halide ions in solution. Although the membrane does not contain any halide, it is capable of determining silver or halide ions in diluted or saturated solutions in a quick, reproducible and precise way.

This object is reached with a membrane according to the invention comprising silver sulfide doped with an ion capable of forming either with $Ag^+$, or with $S^{2-}$ a highly insoluble salt, i.e.; significantly more insoluble than the species in solution.

By "doped silver sulfide", it is meant that the doping agent/silver sulfide ratio is less than 5% mol/mol, and preferably about 1% mol/mol and that the doping agent does not take part in the electrochemical equilibrium involved.

Another object of the present invention is to obtain a membrane exhibiting improved mechanical properties and sufficiently resistant to chemicals.

This object is reached with a Ag₂S crystalline membrane doped with an ion forming with $S^{2-}$ or $Ag^+$ a highly insoluble salt, further containing a hydrophobic compound.

Another object of the present invention is to obtain an electrode using said membrane which is of easy use and inexpensive.

This object is reached by mounting said membrane so that it is interchangeable.

It is a further object of this invention to prepare a silver halide emulsion using an electrode containing a membrane according to the invention.

DESCRIPTION OF PREFERRED EMBODIMENTS

The electrode according to the invention detects the activity of silver ions or halide ions in solution. In diluted solution, i.e. for concentrations lower than $10^{-3}$ mole/l, the ion activity is substantially equal to the concentration. Beyond $10^{-3}$ mole/l, a correction factor should be applied. Between the electrode and the reference element, a potential difference is created, which varies as the activity of the ion to which said membrane is selective. The relationship between the ion activity and the potential measured is logarithmic:

$$E = E_a + 2.3 \, RT/nF \log A \quad \text{(Nernst equation)}$$

where:

E is the potential measured, $E_a$ is the potential fraction specific of the reference electrode and the internal solutions, 2,3 RT/nF is a constant of the system, A is the activity of the ion in solution.

The electrode according to the invention provides quick and precise responses in accordance with Nernst equation in most of the diluted or saturated solutions. It allows to detect activities of $Ag^+$ ions as low as $10^{-16}$ mole/l in silver halide solutions and of $Ag^+$ ions as low as $10^{-5}$ mole/l in AgNO₃ solutions or of $X^-$ ions as low as $10^{-5}$ mole/l in halide solutions.

Figure 1:
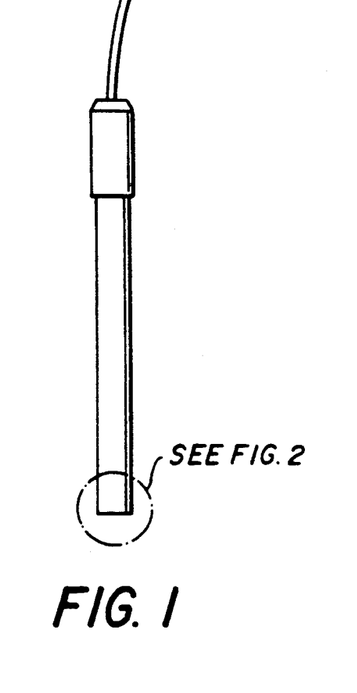
FIG. 1 is an elevation of an electrode.
Figure 2:
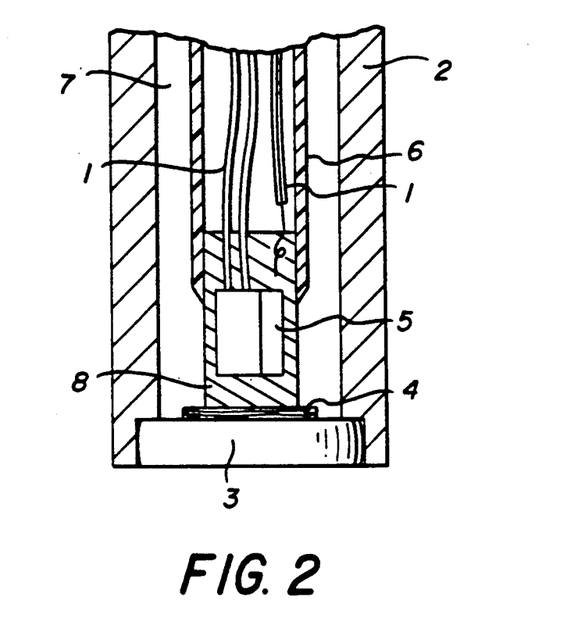
FIG. 2 is a sectional detail of the portion of the electrode within area A.

In an embodiment of the present invention illustrated in FIGS. 1 and 2, the electrode is made of an elongated hollow tubular container of resin, also referred to as an electrode housing, (2) comprising:

a) a reference electrode (8), comprised of a mixture 90:10 w/w of silver and resin, immersed in a AgNO₃ solution of known concentration (7), b) the Ag₂S membrane (3) according to the invention, tightly mounted at an end of the electrode housing. For example, the membrane can be fixed with an adhesive to the electrode housing, in which case the electrode housing forms with the membrane the interchangeable part, or be mounted with a O-ring, for example a silicone joint, in which case it is the membrane itself which is interchangeable.

Practically, the reference electrode is placed as close as possible to the membrane, for example, by inserting a paper slice (4) having a thickness lower than 0.2 mm between the membrane and the reference electrode, to avoid the shift of potential due to the difference of temperature between the membrane and the reference electrode. Alternatively, a temperature sensor (5), for example a silicon sensor can be placed in the resin to automatically correct the potential shift. A sheath (6) of thermoplastic resin insulate the electrical connections (1) coming from the temperature sensor (5) and the reference electrode (8) from the reference solution (7).

Figure 3:
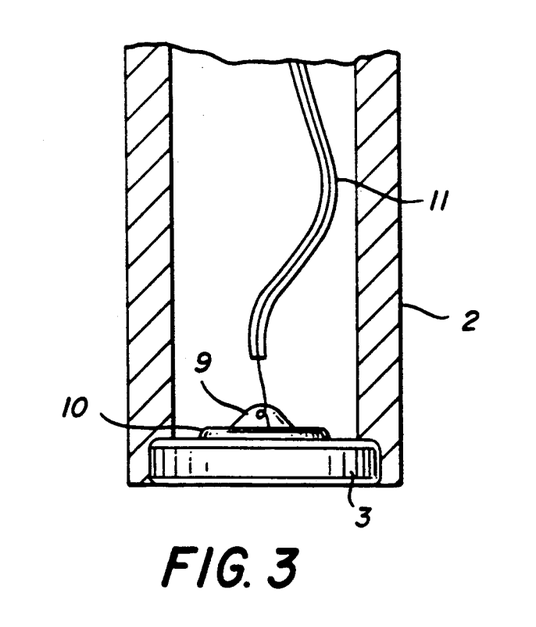
FIG. 3 is a detail of a varied electrode construction.

In another embodiment, the electrode does not contain a reference electrolyte, as illustrated in FIG. 3. One face of the membrane according to the invention (3) is contacted with the test solution, the other face being coated with silver metal (10) and appropriately connected, e.g. through a tin weld (9) to a metal wire (11) itself connected to the measuring system. The silver metal layer can constitute the reference system.

In still another embodiment (not represented) the electrolyte slowly flows, in a controlled way through the membrane.

When operating, the selective electrode is connected to one terminal of a high impedance millivoltmeter ($>10^{12}\,\Omega$), the other terminal of which is connected to the reference electrode through a saline bridge.

The process of preparing the membrane comprises the following steps:

1) silver sulfide is coprecipitated with less than 5 mol percent of doping agent, the resulting coprecipitate is filtered, washed and dried, 2) the coprecipitate being homogenized;

3) a small amount of said homogenized coprecipitate is compacted at ambient temperature and under pressure to obtain a practically imporous thin pellet; and 4) the pellet is subjected to a thermal treatment at a temperature between 90° C. and 150° C.

In a preferred embodiment the coprecipitate is mixed homogenously with a hydrophobic material.

The first step in the preparation of the membranes is the coprecipitation of Ag₂S and the doping agent.

The doping agent allows the creation of defects in the structure of Ag₂S crystal and on its surface, to obtain the necessary high conductivity.

Practically, the doping agent is selected from among cations or anions which form highly insoluble salts with $Ag^+$ or $S^{2-}$, i.e. significantly more insoluble than the salt species in solution, which in the present case are mainly comprised of silver halide. If the solubility constant ks of a salt is defined as the product of the activities of the ions forming the salt, the solubility product pks, as the reverse (negative) of the logarithm of the solubility constant, a salt is considered as "significantly more insoluble" than another salt, when its solubility constant ks is lower by at least a $10^{-3}$ factor to the solubility constant of said other salt, or when its solubility product pks is higher by at least 3 units than that of the other salt. Thus, as doping agent, will be selected an anion or a cation forming with $Ag^+$ or $S^{2-}$, a salt having a pks at least higher than 20, if, as is often the case, the most insoluble species in the solution is AgI ($pks_{AgI}$ about 17 at 25° C.), and preferably higher than $Ag_2S$ pks which is about 49 at 18° C. For example, chalcogenide anions such as $Se^{2-}$, $Te^{2-}$ or metal cations such as $Pb^{2+}$, $Cd^{2+}$, $Cu^{2+}$, $Hg^{2+}$, $Pd^{2+}$, $Tl^{3+}$, $Au^{3+}$, $Rb^+$ can be used. A particularly preferred cation is $Hg^{2+}$.

The amount of doping agent may vary in a large range depending on the nature of the doping agent itself, but remains lower than 5 mol percent. If the doping agent is $Hg^{2+}$, a preferred range is 0.5-5 mol percent based on $Ag_2S$ moles and more preferably of about 1 mol percent based on $Ag_2S$ moles.

The doping agent is incorporated in $Ag_2S$ by coprecipitation. For example, if the dopant is $Hg^{2+}$, $S^{2-}$ and $Ag^+$ are introduced by double jet in the form of salts, in the presence of a $S^{2-}$ excess and in basic medium, preferably at a pH > 10, $Hg^{2+}$ being introduced in the form of a salt in the $Ag^+$ jet.

The coprecipitate obtained is in the form of composite crystals of $Ag_2S$ and doping agent, for example, if the doping agent is $Hg^{2+}$, the coprecipitate is comprised of silver sulfide, mercuric sulfide and mixed silver and mercury sulfides.

After washing and drying, the precipitate is homogenized for several minutes to break the crystal aggregates, without grinding the crystals. Preferably, the coprecipitate is mechanically mixed with a hydrophobic compound in the form of fine particles, for example, dry mixed or mixed in solvent medium in a ball-mill. Alternatively there can be formed a dispersion of particles of homogenized coprecipitate and hydrophobic material in an organic solvent, such as chloroform. In the latter case, the solvent is allowed to evaporate while the dispersion is maintained.

This hydrophobic compound allows reduction of the membrane porosity, improvement of its mechanical properties and lubrication of its surface. Any hydrophobic compound, in the form of particles, having a size close to $Ag_2S$ crystals, i.e. <25 µm, can be used, provided that the compound is inert, i.e. is resistant to the chemicals contained in the solutions to be detected and is resistant to the temperatures of thermal treatment—i.e. resistant to a temperature of about 150° C.—as fluorocarbon polymers or halohydrocarbon polymers such as poly(tetrafluoroethylene), poly(hexafluoropropylene) or poly(vinylidene fluoride). A preferred polymer is poly(tetrafluoroethylene) Teflon TM (marketed by Dupont de Nemours). For example, 0.5 to 20% w/w, preferably 1% w/w of Teflon TM 701N having a particle size of 20 µm, or 0.5 to 20% w/w, preferably 2.5%-3% w/w of Teflon TM DLX6000 having a particle size of 1 µm, can be used.

The following step consists in compacting the resulting homogenized coprecipitate or the homogenous mixture comprising the coprecipitate and the hydrophobic compound, to obtain a dense and practically imporous pellet having an optimum conductivity and good mechanical properties and also to avoid gas voids. During that step, distortion of crystals should be avoided, which could result in a loss in the membrane conductivity. The compacting is realized in an hydraulic press according to a pressure cycle. The powder is compacted under vacuum between two surfaces of polished steel. The variation of the pressure P expressed in kiloPascals versus time t expressed in minutes is the following:

$$P = 5 \times 10^2 + b.(t)^a \times 10^2$$

where a is comprised between 1 and 2 and b is from 5 to 15.

The maximum pressure is from $55 \times 10^2$ kPa to $155 \times 10^2$ kPa.

Then the pellet is allowed to rest 1 to 15 minutes for stabilization.

Last a thermal treatment allows homogenization of the crystalline phase (by coalescense). The treatment is conducted in oil or preferably in air at a temperature between 90° C. and 150° C. for 6 to 24 h.

The membrane obtained is in the form of a dark grey pellet having a diameter of about 10 mm and a thickness of about 0.8 mm. It is substantially non-porous, its density varies from 6.55 to 7.13 and its surface does not exhibit any asperity.

EXAMPLES

The following examples 1-3 relate to the preparation of the membranes.

EXAMPLE 1

A first solution containing $AgNO_3$ (0.98 mole), $Hg(CH_3COO)_2$ (0.01 mole), acetic acid (0.035 mole) in 100 g water and a second solution containing $Na_2S,9H_2O$ (0.5 mole) and sodium hydroxide ($2.5 \times 10^{-3}$ mole) in 919 g water, were prepared. Under stirring, both solutions were introduced by double jet in a kettle containing $Na_2S,9H_2O$ (0.156 mole) and sodium hydroxide (0.22 mole) in 1.5 l water at 50° C. The precipitation took place for 60 minutes at a pH of 11.3. Then the coprecipitate was filtered, thoroughly washed with water, and dried with acetone.

A sample containing 5 g of precipitate was taken, and 1% w/w of Teflon TM 701N was added. The mixture was dry milled in a ball mill at ambient temperature for 15 minutes. An homogeneous powder was obtained.

423 mg of said powder was introduced in a pressing mould between two discs of polished steel. A pressure was applied to the hydraulic press according to a pressure cycle, the pressure varying from 0 to $55 \times 10^2$ kPa. The membrane was allowed to rest for 15 minutes in the press. Its weight was 420 mg, its diameter 10 mm, its thickness 0.764 mm. Then a thermal treatment was conducted in the air at 140° C. for 14 hours and 30 minutes.

EXAMPLE 2

A membrane was prepared according to the procedure of Example 1, except that 2.5% of Teflon TM DLX6000 was used instead of Teflon TM 701N. The membrane weight was 0.423 mg, its thickness 0.793 mm.

EXAMPLE 3

A membrane was prepared according to the procedure of Example 1, except that 2.5% of Teflon TM DLX 6000 was used. The weight of the membrane was 0.423 mg and its thickness 0.814 mm.

EXAMPLE 4

A membrane was prepared according to the procedure of Example 1, except that 3% of Teflon TM DLX6000 was used. The weight of the membrane was 0.421 mg and its thickness 0.791 mm.

EXAMPLE 5

Two electrodes of the type represented in FIGS. 1 and 2 were made, comprising the membrane of Example 1 and the membrane of Example 2, respectively, by gluing the membranes to the lower end of the electrode housing. The whole membrane/electrode housing was then interchangeable.

Between two measurements, the electrode was rinsed with water and wiped to dry it.

To calibrate said electrodes, they were placed in saturated or non-saturated AgX solutions containing a known amount of KX, the ionic strength of which being adjusted to 0.1 with $KNO_3$. Thus, the responses given by the electrodes for known amounts of KCl in saturated or non-saturated solutions of AgCl, of KBr in saturated or non-saturated solutions of AgBr, of KI in saturated or non-saturated solutions of AgI, respectively, were noted.

FIGS. 4 to 7 show the response of the electrodes, expressed as VAg versus pAg ($-\log$ activity $Ag^+$ ions), in solutions at 40° C. for increasing concentrations of halides. Thus from the left to the right on FIGS. 4 to 7, the VAg are those obtained for chloride concentrations of $10^{-5}$, $10^{-4}$, $10^{-3}$, $10^{-2}$, $10^{-1}$ mole/l, respectively (pAg about from 4 to 8), for bromide concentrations of $10^{-5}$, $10^{-4}$, $10^{-3}$, $10^{-2}$, $10^{-1}$ mole/l, respectively (pAg about from 6.5 to 10.5), for iodide concentrations of $10^{-4}$, $10^{-3}$, $10^{-2}$, $10^{-1}$ mole/l, respectively (pAg about from 11 to 14).

Figure 4:
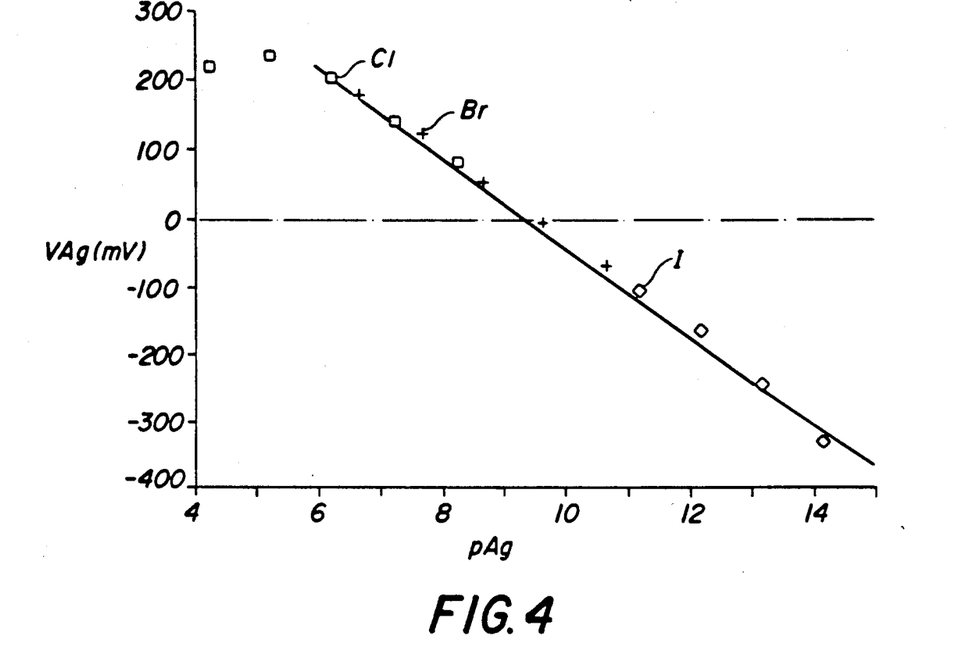
FIGS. 4 to 8 inclusive are plots of VAg in mV versus pAg.

FIG. 4 shows the response of the electrode comprising membrane 1 in saturated solutions of AgCl, AgBr, AgI, respectively.

Figure 5:
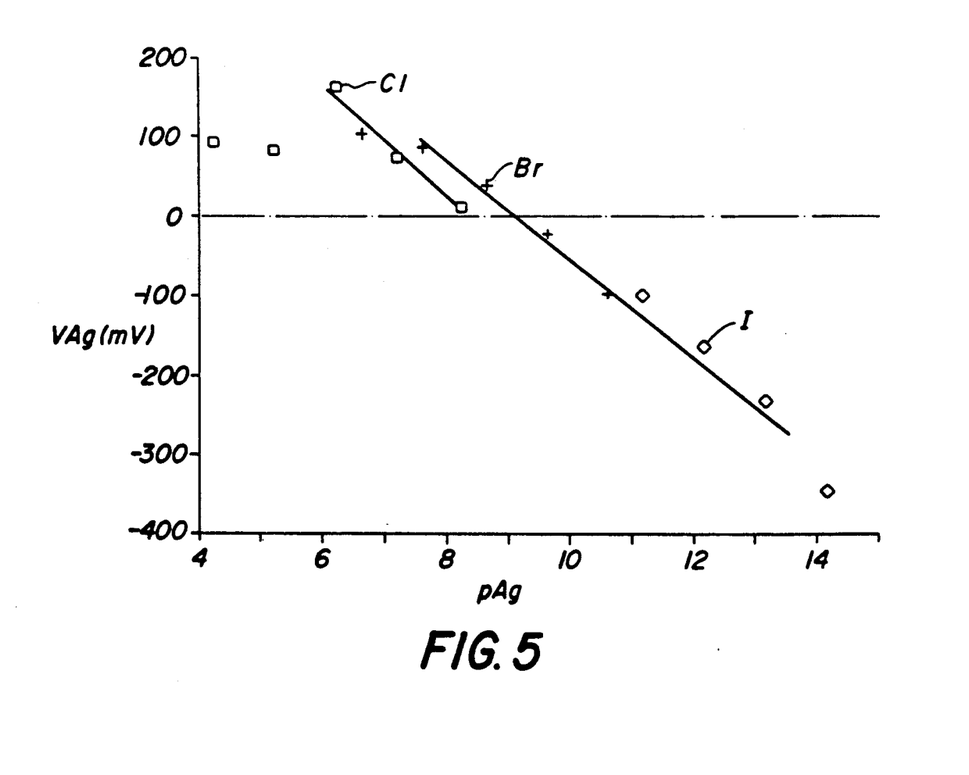

FIG. 5 shows the response of the electrode comprising membrane 1 in non-saturated solutions of AgCl, AgBr, AgI, respectively.

Figure 6:
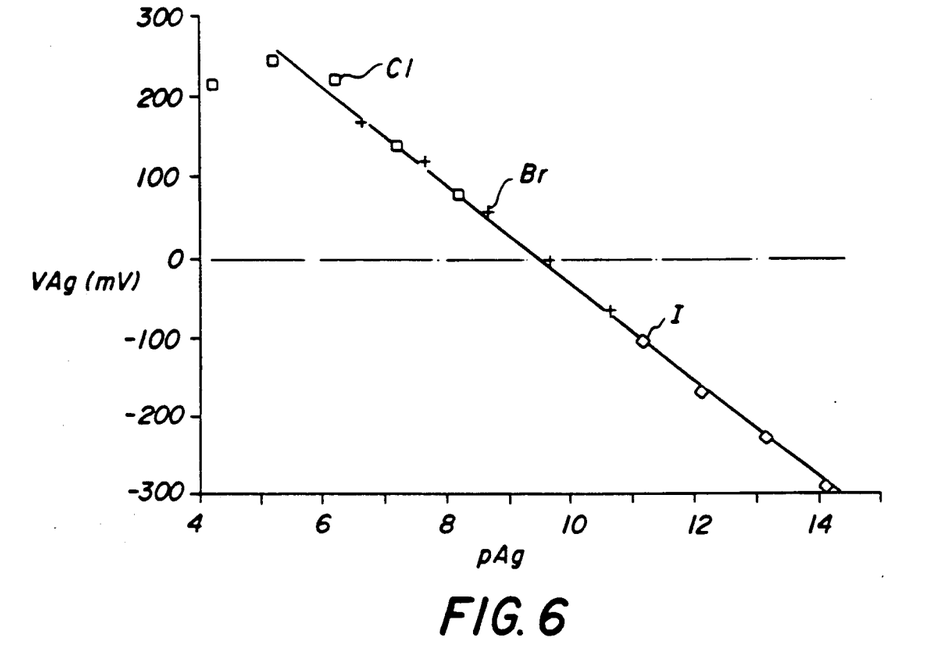

FIG. 6 shows the response of the electrode comprising membrane 2 in saturated solutions of AgCl, AgBr, AgI respectively.

Figure 7:
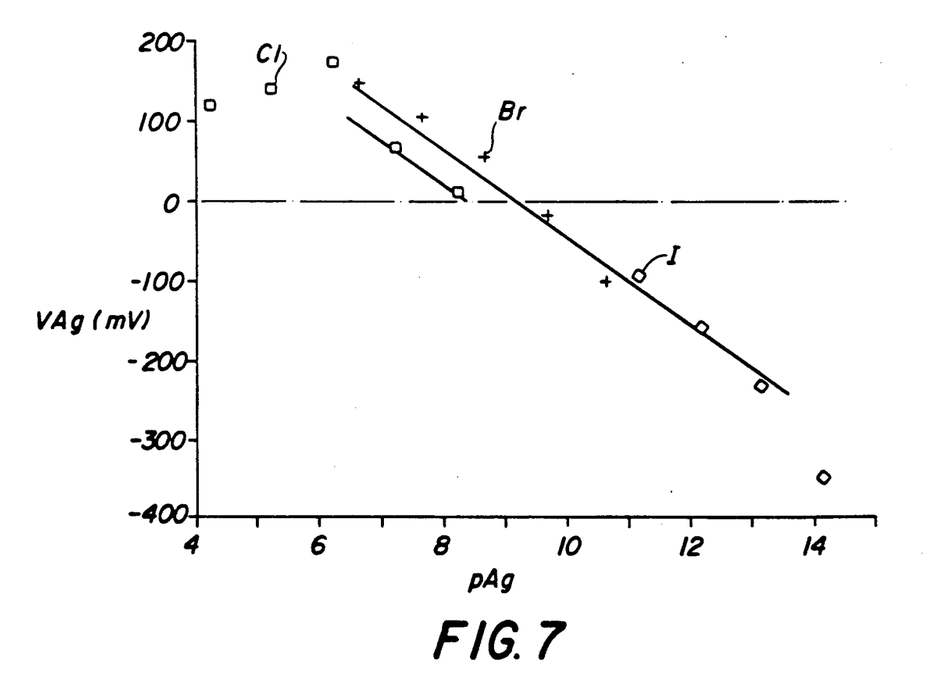

FIG. 7 shows the response of the electrode comprising membrane 2 in non-saturated solutions of AgCl, AgBr, AgI, respectively.

In any case, three distinct areas can be observed: the chloride area where chloride concentration is comprised between $10^{-5}$ and $10^{-3}$ mole/l ($4 < pAg < 6.5$), the bromide area where bromide concentration is comprised between $10^{-3}$ and $10^{-1}$ mole/l ($8.5 < pAg < 11$), the iodide area where iodide concentration is comprised between $10^{-4}$ and $10^{-1}$ mole/l ($11 < pAg < 14$). An area common to chlorides $10^{-3} - 10^{-1}$ mole/l and bromides $10^{-5} - 10^{-3}$ mole/l ($6.5 < pAg < 8.5$) can also be observed.

It can be seen from FIGS. 4 and 6 that in saturated solutions, nernstein responses (i.e. a linear relationship between VAg and the pAg, according to Nernst equation) are obtained for chloride concentrations from $10^{-3}$ to $10^{-1}$ mole/l ($6 < pAg < 8$), bromide concentrations from $10^{-5}$ to $10^{-1}$ mole/l ($6.5 < pAg < 10.5$), iodide · concentrations from $10^{-4}$ to $10^{-1}$ mole/l ($11 < pAg < 14$).

From FIGS. 5 and 7 it can be seen that the nernstian behaviour in non-saturated solutions is encountered mainly for chloride concentrations from $10^{-3}$ to $10^{-1}$ mole/l ($6 < pAg < 8$), bromide concentrations from $10^{-4}$ to $10^{-1}$ mole/l ($8.5 < pAg < 10.5$) and iodide concentrations from $10^{-2}$ to $10^{-4}$ mole/l ($11 < pAg < 13$).

EXAMPLE 6

An electrode of the type illustrated in FIG. 3, was made by coating one face of the membrane prepared in Example 3 with a layer of metal silver containing polymer and by connecting said layer by means of a tin welding to a copper wire, itself connected to the electrochemical cell arrangement. The whole wire/coated membrane was placed in a resin cylinder and was easily interchangeable.

Figure 8:
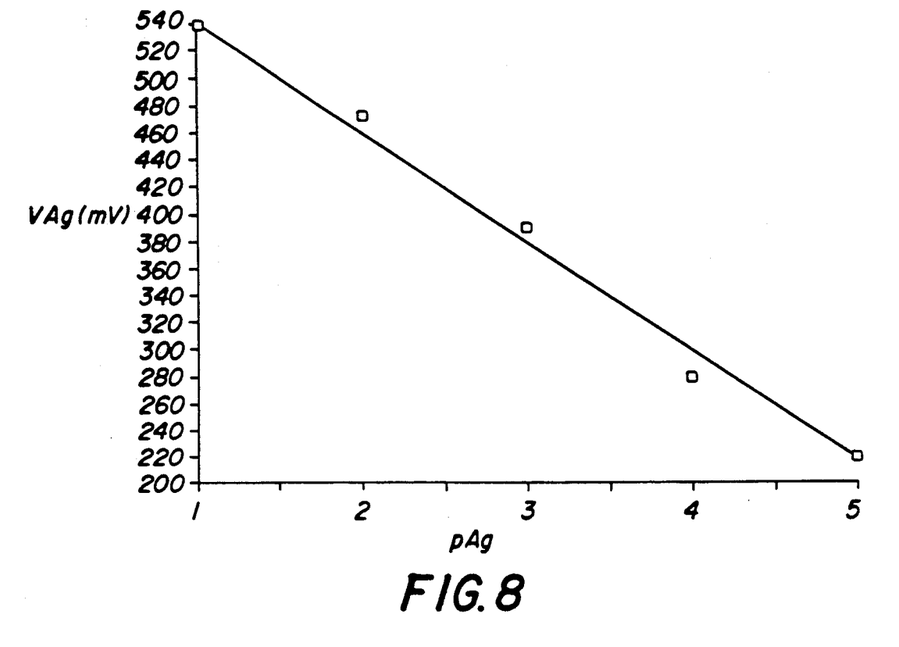

FIG. 8 illustrates the response of said electrode in $AgNO_3$ solutions, the concentrations of which were $10^{-1}$, $10^{-2}$, $10^{-3}$, $10^{-4}$, $10^{-5}$ mole/l, respectively ($1 < pAg < 5$).

Once again the responses observed are substantially nernstian, for all the concentrations.

EXAMPLE 7

An electrode of the type represented on FIGS. 1 and 2 was made, comprising the membrane of Example 1 by gluing the membrane to the lower end of the electrode housing. The whole membrane/electrode housing was then interchangeable.

Between two measurements, the electrode was rinsed with water and wiped to dry it.

To test the electrode according to the invention during the emulsion precipitation, said electrode and a conventional Ag/AgBr silver billet electrode were placed abreast in the kettle.

Figure 9:
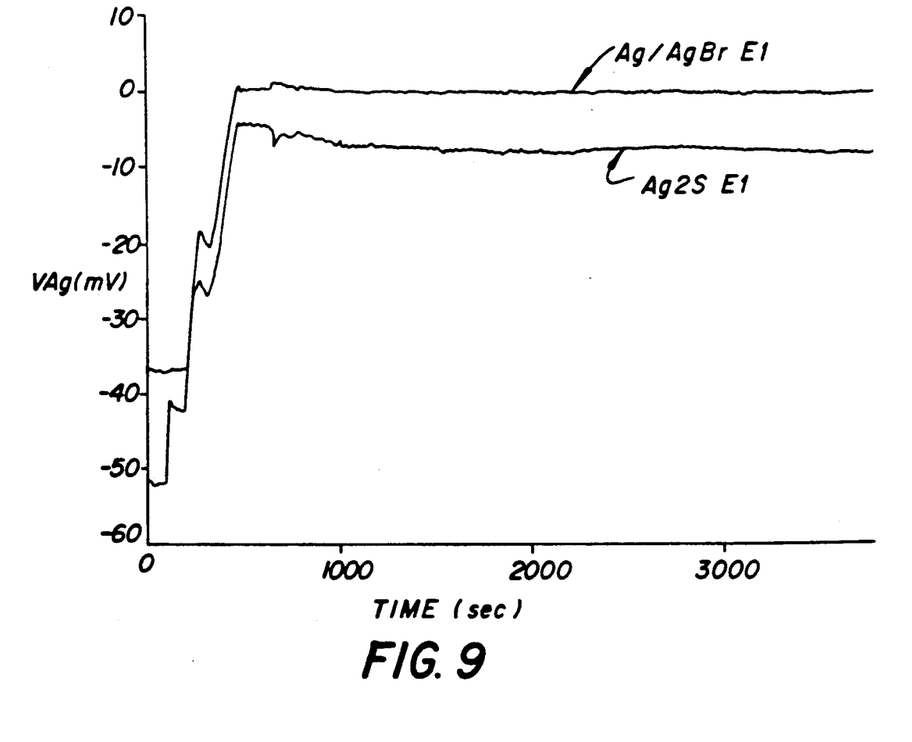
FIGS. 9 and 10 are plots of Vag in mV versus time in seconds and minutes, respectively.

FIG. 9 allows comparison of the response of the electrode comprising the membrane of Example 1 with a conventional Ag/AgBr electrode during the precipitation of a silver bromide emulsion. During the precipitation the VAg in the kettle varied from about $-50$ mV to about 0 mV. Said emulsion was prepared by double jet by introducing potassium bromide and silver nitrate in the gelatin solution. On the curve, several peaks can be observed corresponding in the order to the appearance of the first seed crystals, to the temperature raise, and to a gelatin introduction, then the precipitation was run at a constant VAg of $-8$ mV. With the electrode according to the invention, a response was obtained before the silver bromide precipitated, and supersaturation was clearly noticeable before the appearance of the first seed crystals, while the Ag/AgBr electrode does not distinguish it. The detection of the supersaturation can be very useful in detecting the beginning of the precipitation.

EXAMPLE 8

An electrode, as illustrated in FIG. 3, was made by coating one face of the membrane prepared in Example 2 with a layer of silver metal containing polymer and by connecting the layer by means of a tin welding to a copper wire, itself connected to the electrochemical cell arrangement. The whole wire/coated membrane was placed in a resin cylinder and was easily interchangeable.

Said electrode according to the invention was tested as above during the precipitation of an emulsion.

Figure 10:
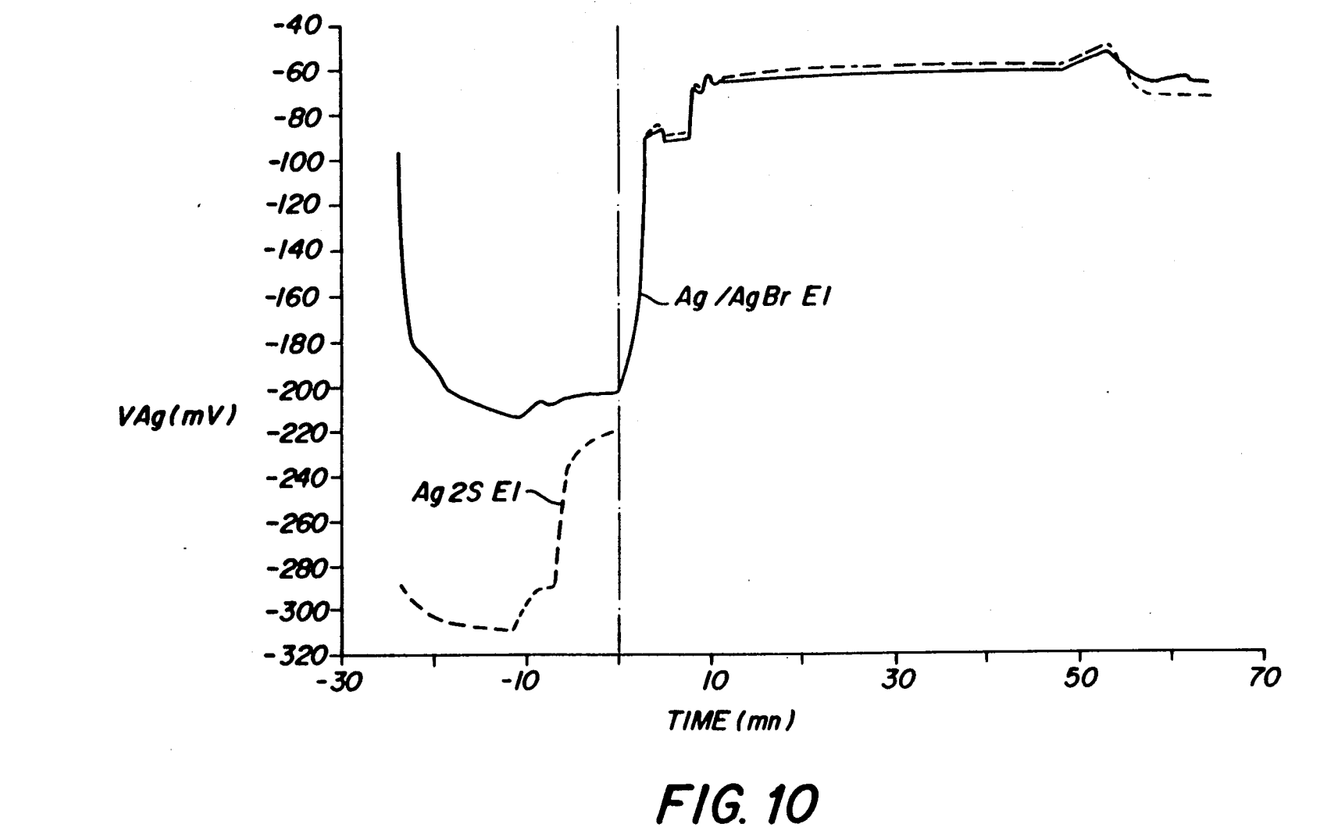

FIG. 10 allows to compare the response of the electrode comprising the membrane of Example 2 with a Ag/AgBr electrode during the precipitation of a silver bromoiodide emulsion where the VAg varies from −310 mV to −50 mV. First at time t=0, silver nitrate was introduced in the kettle containing a small amount of potassium iodide, then potassium bromide and potassium iodide were introduced to precipitate silver bromoiodide.

It can be observed that at the beginning (before t=0) when the two electrodes tend to equilibrium, the Ag/AgBr electrode loses bromide (VAg varying rapidly from −100 mV to −210 mV) while the electrode according to the invention gives quickly a response.

It can be observed that in Examples 7 and 8, the responses of the electrodes according to the invention are very close to the responses of conventional Ag/AgBr electrodes, however the electrodes according to the invention are more sensitive to the nucleation processes. Besides, in the case of the precipitation of emulsions containing iodide, the electrodes according to the invention can be reused after a simple rinsing while Ag/AgBr prior art electrodes must be replated.

The invention has been described in detail with particular reference to preferred embodiments thereof, but it will be understood that variations and modifications can be effected within the spirit and scope of the invention.

What is claimed is:

1. A membrane sensitive to silver or halide ions in a solution containing one or more salt species, said membrane comprising silver sulfide containing less than 5 mole percent, based on $Ag_2S$, of a doping agent capable of forming, either with $Ag^+$ or with $S^{2-}$, a salt having a pks at least 3 units higher than the pks of the most insoluble of said salt species in solution.

2. Membrane according to claim 1 wherein said doping agent is selected among $Rb^+$, $Hg^{2+}$, $Pd^{2+}$, $Tl^{3+}$, $Au^{3+}$, $Se^{2-}$, $Te^{2-}$.

3. A membrane according to claim 2 wherein said doping agent is $Hg^{2+}$.

4. A membrane comprised of $Ag_2S$ containing $Hg^{2+}$ as a doping agent, wherein the molar ratio of $Hg^{2+}$ to $Ag_2S$ is about 1%.

5. A membrane according to claims 1 to 4 further comprising an inert hydrophobic material.

6. A membrane according to claim 5 wherein said hydrophobic material is a hydrophobic polymer resistant to a temperature of about 150° C.

7. A membrane according to claim 6 wherein said hydrophobic polymer is poly(tetrafluoroethylene), poly(hexafluoropropylene) or poly(vinylidene fluoride).

8. A membrane according to claim 7 wherein the polymer is poly(tetrafluoroethylene) and the weight ratio of poly(tetrafluoroethylene) to silver sulfide is in the range of from 0.5 to 20%.

9. A membrane according to claim 8 wherein said poly(tetrafluoroethylene) is in the form of particles having a size less than 25 μm.

10. Electrode to measure the activity of silver or halide ions in solution, comprising the membrane defined in any one of claims 1 to 9 inclusive.

11. Use of the electrode according to claim 10 to monitor the precipitation of silver halides during the preparation of photographic emulsions, said emulsions being pure halide or mixed emulsions.

12. A membrane sensitive to the silver or halide ions of a silver halide salt having a higher solubility than at least one other silver halide salt of a differing halide in a solution containing silver ions and ions of both of the halides, said membrane comprising silver sulfide containing less than 5 mole percent, based on silver sulfide, of a doping agent capable of forming, either with $Ag^+$ or with $S^{2-}$, a salt having a pks at least 3 units higher than the pks of the other silver halide.

13. A membrane sensitive to the silver or halide ions of a silver halide salt having a higher solubility than silver iodide in a solution containing both the silver halide salt and silver iodide, said membrane comprising silver sulfide containing less than 5 mole percent, based on silver sulfide, of a doping agent capable of forming, either with $Ag^+$ or with $S^{2-}$, a salt having a pks at least 3 units higher than the pks of silver iodide.

* * * * *